(12) United States Patent
Al Askar

(10) Patent No.: US 9,314,243 B1
(45) Date of Patent: Apr. 19, 2016

(54) GINGIVAL GRAFT STABILIZER

(71) Applicant: KING SAUD UNIVERSITY, Riyadh (SA)

(72) Inventor: Mansour Hamad Al Askar, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/680,002

(22) Filed: Apr. 6, 2015

(51) Int. Cl.
- *A61B 17/04* (2006.01)
- *A61C 1/08* (2006.01)
- *A61C 8/02* (2006.01)

(52) U.S. Cl.
CPC .............. *A61B 17/0482* (2013.01); *A61C 1/082* (2013.01); *A61C 8/0006* (2013.01)

(58) Field of Classification Search
CPC ........... A61B 17/0482; A61B 17/0483; A61B 17/320708; A61B 17/1659; A61B 17/1679; A61B 17/1688; A61B 17/1697; A61B 17/1796; A61B 17/50; A61B 17/24; A61B 17/244; A61B 17/28; A61B 17/30; A61B 17/26; A61B 17/22; A61B 17/0469; A61B 2017/320716; A61B 2017/505; A61B 2017/248; A61B 15/0081; A61B 1/24; A61C 8/0006; A61C 8/0089; A61C 3/00; A61C 3/10; A61C 3/08; A61C 13/12; A61C 9/0033; A61C 19/004; A61C 19/005; A61C 1/082; A61F 11/006; A61F 13/38; B25B 9/02

See application file for complete search history.

(56) References Cited

U.S. PATENT DOCUMENTS

| | | | |
|---|---|---|---|
| 4,698,019 A * | 10/1987 | Martin | 433/144 |
| 2005/0100860 A1 * | 5/2005 | Kameli | 433/144 |
| 2006/0029906 A1 * | 2/2006 | Hill | A61C 3/00 433/141 |
| 2007/0202460 A1 * | 8/2007 | Chao | 433/141 |
| 2010/0062393 A1 * | 3/2010 | Latiolals | A61C 3/00 433/141 |
| 2011/0143312 A1 | 6/2011 | McAdams et al. | |
| 2013/0101959 A1 | 4/2013 | Lee | |

* cited by examiner

*Primary Examiner* — Jocelin Tanner
(74) *Attorney, Agent, or Firm* — Richard C. Litman

(57) ABSTRACT

A gingival graft stabilizer has an elongate member and slanted arms extending from opposing ends of the elongate member. An anterior guide extends from one of the arms and a posterior guide extends from the other arm. The anterior guide includes spaced protrusions extending from an upper end of the anterior guide. The posterior guide includes spaced protrusions extending from opposing sides of the posterior guide. During suturing of a gingival graft, a dental surgeon holding the elongate member can stabilize and position a gingival graft on anterior gingiva using the anterior guide or on posterior gingiva using the posterior guide. Sutures can be made in the spaces between and around the protrusions of the anterior guide or the posterior guide.

10 Claims, 4 Drawing Sheets

GINGIVAL GRAFT STABILIZER

BACKGROUND OF THE INVENTION

1. Field of the Invention

The present invention relates to a tool that can be used for periodontal plastic surgery, and particularly to a gingival graft stabilizer for use in a suturing procedure.

2. Description of the Related Art

A Gingival Graft (GG) is a surgical procedure frequently used in periodontics to increase the amount of keratinized tissue surrounding a tooth or a dental implant. Keratinized tissue plays a major role around teeth and dental implants, helping in maintaining oral hygiene. This surgical technique can be considered an oral or periodontal plastic surgery and is relatively delicate. The process involved in the healing of this type of gingival graft can depend on many factors, including stabilization of the graft during suturing.

Gingival graft stabilization (GGS) is relatively important in periodontal plastic surgery. Current approaches and devices have drawbacks, such as graft folding, or are not effective. Dental pliers, for example, do not provide proper stabilization. Further, traditional suturing techniques can result in increased trauma to the graft during suturing.

Thus, a gingival graft stabilizer addressing the aforementioned problems is desired.

SUMMARY OF THE INVENTION

A gingival graft stabilizer has an elongate member and slanted arms extending from opposing ends of the elongate member. An anterior guide extends from one of the arms and a posterior guide extends from the other arm. The anterior guide includes spaced protrusions extending from an upper end of the anterior guide. The posterior guide includes spaced protrusions extending from opposing sides of the posterior guide. During suturing of a gingival graft, a dental surgeon holding the elongate member can stabilize and position a gingival graft on anterior gingiva using the anterior guide or on posterior gingiva using the posterior guide. Sutures can be made in the spaces between and around the protrusions of the anterior guide or the posterior guide.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
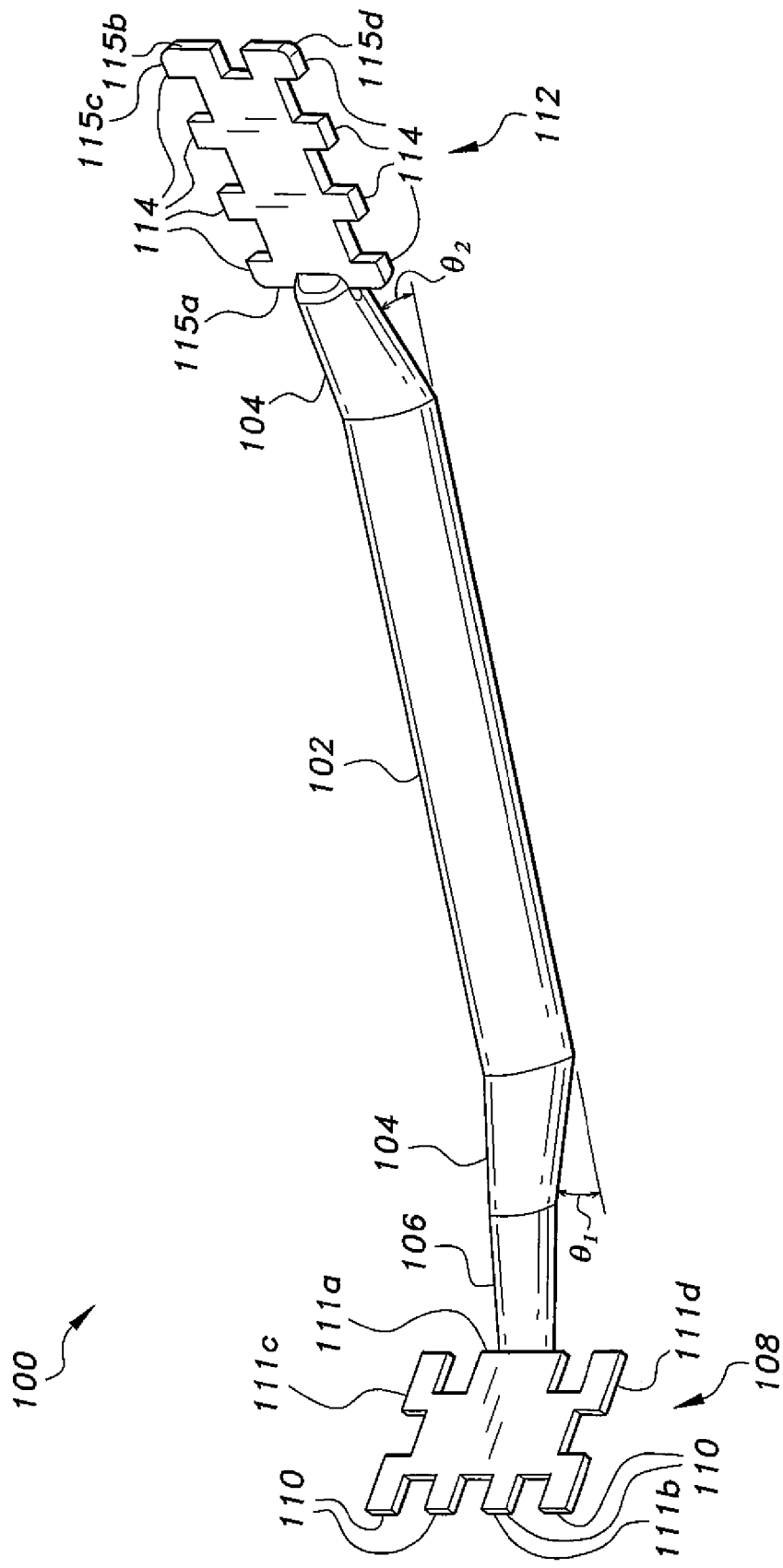
FIG. 1 is a perspective view of a gingival graft stabilizer according to the present invention.
Figure 2A:
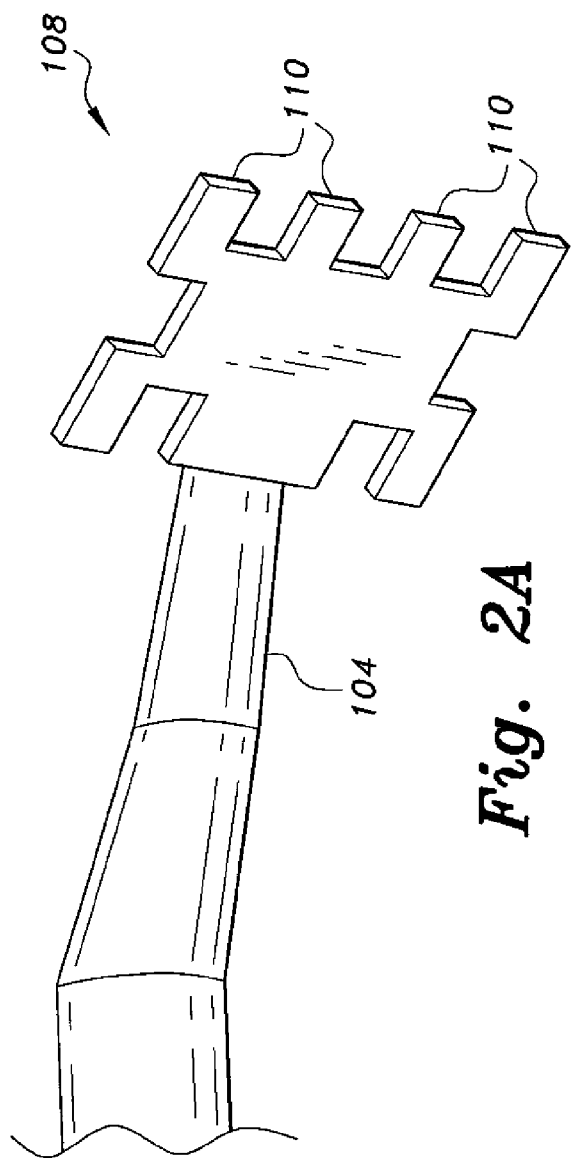
FIG. 2A is a sectional view of an anterior guide of a gingival graft stabilizer according to the present invention.
Figure 2B:
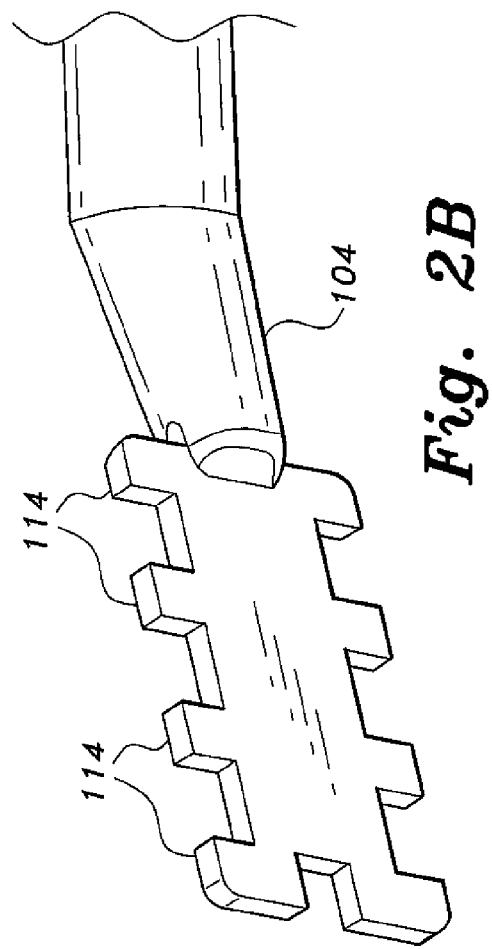
FIG. 2B is a sectional view of a posterior guide of a gingival graft stabilizer according to the present invention.

Referring to FIGS. 1-4, a gingival graft stabilizer 100 is shown. As shown in FIG. 1, the gingival graft stabilizer 100 has an elongate member 102. Attached to opposing ends of the elongate member 102 are arms 104. Each arm 104 extends upward at a slant or an angle from the elongate member 102. For example, when the elongate member is positioned on a horizontal support surface, an angle $\theta_1$ can be formed between one of the arms and the horizontal support surface and an angle $\theta_2$ can be formed between the other arm and the horizontal support surface, as shown in FIG. 1. The angles $\theta_1$ and $\theta_2$ can be the same or different from one another. The angles θ1 and θ2 can be less than 90 degrees, e.g., 30 degrees or 45 degrees. An anterior guide 108 extends from one of the arms 104 and a posterior guide 112 extends from the other arm 104. The elongate member 102 can be held by a user, such as a dentist, to operate, manipulate, and control the gingival graft stabilizer 100. The gingival graft stabilizer 100 can be made from any suitable metal or plastic material.

The anterior guide 108 can be generally rectangular with flat upper and lower surfaces. The anterior guide 108 includes a bottom end 111a, an opposing upper end 111b, and opposing sides 111 and 11d, extending between the bottom end 111a and the upper end 111b. The bottom end 111a can be connected to the arm 104 and the upper end 111b can be free. The anterior guide 108 can be angled with respect to the arm 104 from which it extends. The upper end 111a can extend above the bottom end 111b. A plurality of anterior protrusions 110 can extend from the upper end, with openings or spacers defined between the protrusions, i.e., on both sides of each protrusion. The angle of $\theta_1$ can be configured to facilitate contact of the anterior guide 108 with a patient's anterior gingiva. Thus, during suturing of a gingival graft, a user holding the elongate member 102 can use the flat surface of the anterior guide 108 to position and stabilize a graft on gingiva proximate a patient's anterior teeth. Sutures can be made within the spacers or openings between and/or around the plurality of anterior protrusions 110. The plurality of anterior protrusions 110 can, thereby, be used as guiding structures during suturing of a graft for anterior gingiva.

The anterior guide 108 can include an extension piece 106 that extends between and connects the anterior guide and the arm 104. The extension piece 106 can be fixedly or removably attached to the arm 104. The extension piece 106 can extend at an angle with respect to the arm 104, which is different from $\theta_1$. For example, the angle formed between the extension piece 106 and the arm 104 can be greater than $\theta_1$.

The posterior guide 108 can be generally rectangular with flat upper and lower surfaces. The posterior guide 112 includes a bottom end 115a, an opposing upper end 115b, and opposing sides 115c and 115d, extending between the bottom end 115a and the upper end 115b. The bottom end 115a is attached to the arm 104 and the upper end 115b is free. The bottom end 115a can be fixedly or removably attached to the arm 104. The posterior guide 112 can be angled with respect to the arm 104 from which it extends. The upper end 115b can extend above the bottom end 115a. A plurality of posterior protrusions 114 can extend from the opposing sides 115c and 115d, with openings or spacers defined between the protrusions 114. The angle of $\theta_2$ can be configured to facilitate contact of the posterior guide 112 with a patient's posterior gingiva. During suturing of a gingival graft, a user holding the elongate member 102 can use the flat surface of the posterior guide 112 to position and stabilize a graft on gingiva proximate a patient's posterior teeth. Sutures can be made within the spacers or openings between and/or around the plurality of posterior protrusions 114. The plurality of posterior protrusions 114 can, thereby, be used as guiding structures during suturing of a graft for posterior gingiva.

Figure 3:
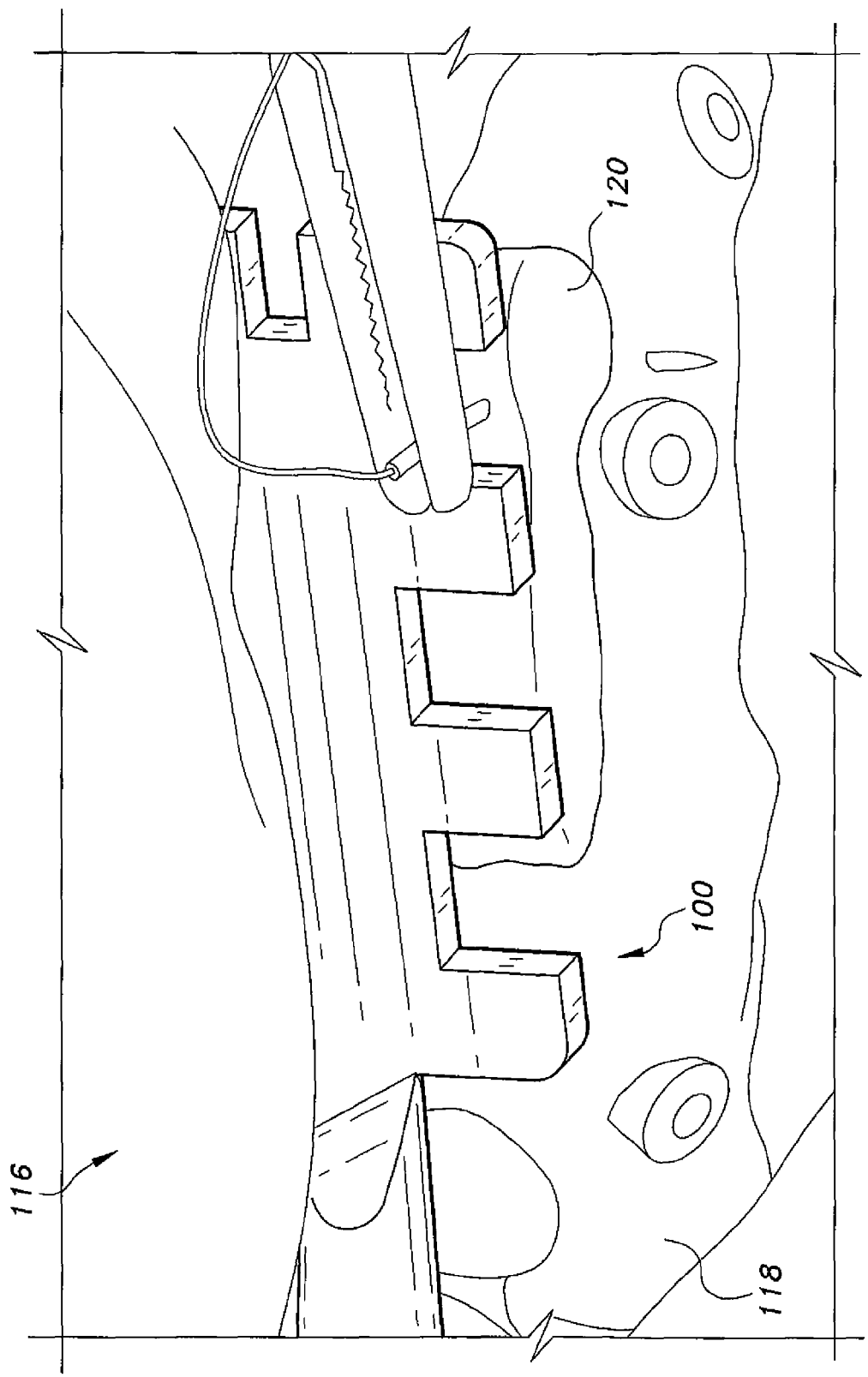
FIG. 3 is an environmental view of a gingival graft stabilizer according to the present invention.
Figure 4:
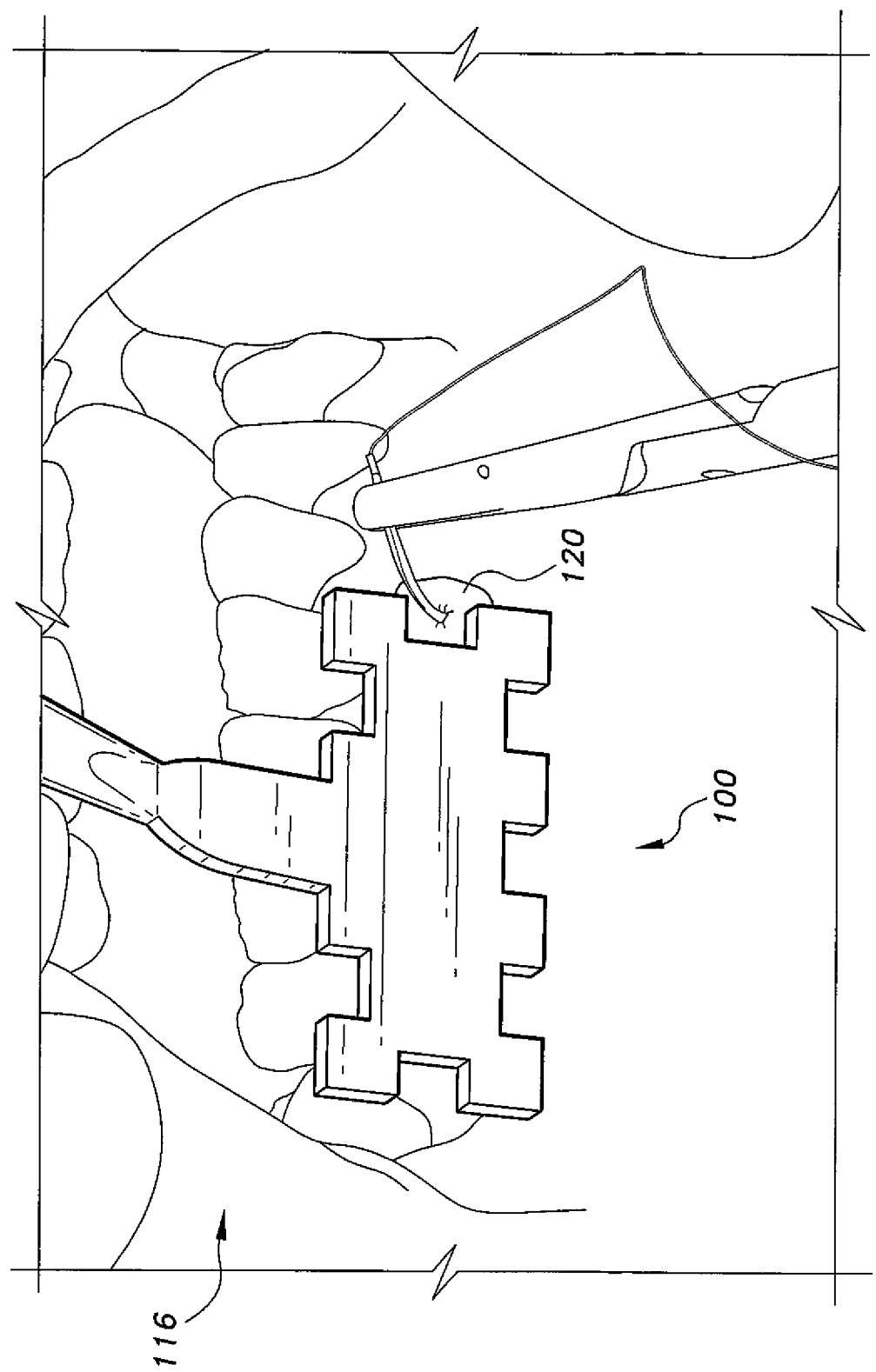
FIG. 4 is an environmental view of a gingival graft stabilizer according to the present invention.

Referring to FIGS. 3-4, the gingival graft stabilizer 100 can be used in a patient's mouth 116 during a gingival graft procedure. Depending on the user's needs, either the flat surface of the anterior guide 108 or the flat surface of the posterior guide 112 can be used to apply a gingival graft 120 to a patient's gingiva 118. Sutures can be made between and around the protrusions 110 and 114 during a suturing technique. The gingival graft stabilizer 100 can be used for grafts associated with dental implants (FIG. 3) and/or with natural teeth (FIG. 4). It should be noted that the gingival graft stabilizer 100 can be used in gingival graft procedures as well as other dental procedures. For example, the gingival graft stabilizer 100 can be used in other periodontal (gum) procedures, oral surgery, or any other dental surgery utilizing graft or membrane applications. Additionally, the gingival graft stabilizer 100 can come in various sizes. For example, the gingival graft stabilizer 100 can be configured to accommodate a shallow vestibule or a deeper vestibule.

The gingival graft stabilizer allows for precision of localizing a graft, such as a gingival graft, in an accurate recipient site of a patient's mouth. The anterior and posterior guides of the gingival graft stabilizer allow for relatively reduced trauma to the graft during a suturing technique. The gingival graft stabilizer allows for quick stabilization and less disrupting continuity of graft nutrition. Further, the gingival graft stabilizer allows for decreased chance of shrinkage of the graft. Generally, decreased shrinkage indicates a successful treatment. The arms of the gingival graft stabilizer can be positioned at multiple angles for efficient access into an anterior region and a posterior region of a patient's mouth.

It is to be understood that the present invention is not limited to the embodiments described above, but encompasses any and all embodiments within the scope of the following claims.

I claim:

1. A gingival graft stabilizer, comprising:
an elongate member, wherein the elongate member has a longitudinal axis;
a pair of arms extending from opposing ends of the elongate member, each of the arms extending at an acutely angled slant with respect to the longitudinal axis of the elongate member, wherein the direction of the slant is the same for each arm;
an anterior guide extending from a first one of the arms, the anterior guide having a flat upper and lower surface and including a bottom end attached to the first arm, an opposing upper end, opposing sides longitudinally extending between the bottom end and the upper end, and a plurality of spaced, anterior protrusions extending peripherally from at least the upper end, wherein the spacing between the protrusions provide openings; and
a posterior guide extending from a second one of the arms, the posterior guide having a flat upper and lower surface and including a bottom end attached to the second arm, an opposing upper end, opposing sides longitudinally extending between the bottom end and the upper end, and a plurality of spaced, posterior protrusions extending peripherally from at least the opposing sides, wherein the spacing between the protrusions provide openings,
whereby the anterior and posterior protrusions provide guiding structures for the suturing of a gingival graft within the openings of the protrusions.

2. The gingival graft stabilizer according to claim 1, wherein the upper end of the anterior guide is above the bottom end of the anterior guide and the upper end of the posterior guide is above the bottom end of the posterior guide.

3. The gingival graft stabilizer according to claim 1, further comprising:
an extension piece, wherein the extension piece extends between and connects the anterior guide with the first arm.

4. The gingival graft stabilizer according to claim 3, wherein the extension piece is slanted with respect to the first arm.

5. The gingival graft stabilizer according to claim 1, wherein the angle formed between the first arm and the elongate member is different from an angle formed between the second arm and the elongate member.

6. The gingival graft stabilizer according to claim 1, wherein the angle formed between the first arm and the elongate member is the same as an angle formed between the second arm and the elongate member.

7. A method of grafting gum tissue comprising using a gingival graft stabilizer to stabilize a graft in a patient's mouth during suturing, the method comprising the steps of:
providing a gingival graft stabilizer including:
an elongate member, wherein the elongate member has a longitudinal axis;
a pair of arms extending from opposing ends of the elongate member, each of the arms extending at an acutely angled slant with respect to the longitudinal axis of the elongate member, wherein the direction of the slant is the same for each arm;
an anterior guide, extending from a first one of the arms, the anterior guide having a flat upper and lower surface and including a bottom end attached to the first arm, an opposing upper end, opposing sides longitudinally extending between the bottom end and the upper end, and a plurality of spaced, anterior protrusions extending peripherally at least the upper end;
a posterior guide extending from a second one of the arms, the posterior guide having a flat upper and lower surface and including a bottom end attached to the second arm, an opposing upper end, opposing sides longitudinally extending between the bottom end and the upper end, and a plurality of spaced, posterior protrusions extending peripherally from at least the opposing sides;
providing a gingival graft;
stabilizing and positioning the gingival graft on a selected anterior or posterior gingiva using either the anterior or posterior guide, respectively; and
suturing the gingival graft to the selected gingiva using the protrusions and openings between the protrusions as guiding structures for the suturing.

8. A gingival graft stabilizer, comprising:
an elongate member, wherein the elongate member has a longitudinal axis;
a pair of arms extending from opposing ends of the elongate member, each of the arms extending at an acutely angled slant with respect to the longitudinal axis of the elongate member;
an anterior guide extending from a first one of the arms, the anterior guide having an flat upper and lower surface and including a bottom end attached to the first arm, an opposing upper end, opposing sides longitudinally extending the bottom end and the upper end, and a plurality of spaced, anterior protrusions extending peripherally from at least the upper end, wherein the spacing between the protrusions provide openings; and
a posterior guide extending from a second one of the arms, the posterior guide having a flat upper and lower surface and including a bottom end attached to the second arm, an opposing upper end, opposing sides longitudinally extending between the bottom end and the upper end, and a plurality of spaced, posterior protrusions extending peripherally from at least the opposing sides, wherein the spacing between the protrusions provide openings, whereby the anterior and posterior protrusions provide guiding structures for the suturing of a gingival graft within the openings of the protrusions.

9. The gingival graft stabilizer according to claim 8, wherein the angle formed between the first arm and the elongate member is different from an angle formed between the second arm and the elongate member.

10. The gingival graft stabilizer according to claim 8, wherein the angle formed between the first arm and the elongate member is the same as an angle formed between the second arm and the elongate member.

\* \* \* \* \*